(12) United States Patent
Sun et al.

(10) Patent No.: US 11,608,454 B2
(45) Date of Patent: Mar. 21, 2023

(54) HIGH PERFORMANCE ADHESIVES; METHODS OF MAKING; AND USE

(71) Applicants: University of Connecticut, Farmington, CT (US); South China University of Technology, Guangzhou (CN)

(72) Inventors: Luyi Sun, Storrs, CT (US); Lan Liu, Guangzhou (CN); Song Chen, Guangzhou (CN)

(73) Assignees: UNIVERSITY OF CONNECTICUT, Farmington, CT (US); SOUTH CHINA UNIVERSITY OF TECHNOLOGY, Guangzhou (CN)

( * ) Notice: Subject to any disclaimer, the term of this patent is extended or adjusted under 35 U.S.C. 154(b) by 970 days.

(21) Appl. No.: 16/410,229

(22) Filed: May 13, 2019

(65) Prior Publication Data

US 2019/0345368 A1  Nov. 14, 2019

Related U.S. Application Data

(60) Provisional application No. 62/670,946, filed on May 14, 2018.

(51) Int. Cl.
*C09J 7/32* (2018.01)
*C09J 129/04* (2006.01)
*C09J 179/04* (2006.01)

(52) U.S. Cl.
CPC ............... *C09J 7/32* (2018.01); *C09J 129/04* (2013.01); *C09J 179/04* (2013.01)

(58) Field of Classification Search
None
See application file for complete search history.

(56) References Cited

U.S. PATENT DOCUMENTS

| 9,272,075 | B2 | 3/2016 | Antoni et al. |
| 9,433,699 | B2 * | 9/2016 | Lee ............... A61L 24/0015 |
| 9,694,344 | B2 | 7/2017 | Song et al. |
| 10,568,984 | B2 * | 2/2020 | Wang ............... A61L 24/043 |
| 2014/0311673 | A1 * | 10/2014 | Zhao ............... C09J 11/02 |
| | | | 525/132 |
| 2016/0355688 | A1 | 12/2016 | Drumheller et al. |

(Continued)

FOREIGN PATENT DOCUMENTS

| WO | 2010091300 A1 | 8/2010 |
| WO | 2014118266 A1 | 8/2014 |
| WO | 2018045905 A1 | 3/2018 |

OTHER PUBLICATIONS

International Search Report for International Application No. PCT/US2019/032000, International Filing Date May 13, 2019, dated Jul. 29, 2019, 5 pages.

(Continued)

*Primary Examiner* — Tae H Yoon
(74) *Attorney, Agent, or Firm* — Cantor Colburn LLP

(57) ABSTRACT

Disclosed are adhesives comprising a first compound comprising three or more 1,2-dihydroxybenzene groups; and a second compound that is a functionalized polymer; wherein the first compound and second compound are in the form of a mixture, and wherein the adhesive has adhesive properties when wet. Additional embodiments to methods of preparing an adhesive, adhesives prepared by the method, and articles prepared from the adhesive are disclosed.

15 Claims, 1 Drawing Sheet

(56) References Cited

U.S. PATENT DOCUMENTS

2017/0156621 A1    6/2017  Bettinger et al.
2018/0053445 A1    2/2018  Sun et al.
2018/0065105 A1    3/2018  Song et al.
2019/0062462 A1*   2/2019  Shi .......................... A61L 27/20

OTHER PUBLICATIONS

Written Opinion for International Application No. PCT/US2019/032000, International Filing Date May 13, 2019, dated Jul. 19, 2019, 6 pages.

Dhand, Chetna et al.; "Bio-inspired crosslinking and matrix-drug interactions for advanced wound dressings with long-term antimicrobial activity"; Biomaterials: 138; 2017, p. 153-168.

Han, Lu et al.; "Mussel-Inspired Adhesive and Tough Hydrogel Based on Nanoclay Confined Dopamine Polymerization"; ACS Nano: 11; 2017; p. 2561-2574.

Mu, Youbing et al.; "Simple but Strong: a Mussel-Inspired Hot Curing Adhesive Based on Polyvinyl Alcohol Backbone"; Macromolecular Rapid Communications: 37; 2016, p. 545-550.

Wilker, Jonathan J.; Positive Charges and Underwater Adhesion; Science: vol. 349:6248; Aug. 7, 2015, p. 582-583.

Wu, Zelin et al.; "Synthesis and Adhesive Property Study of a Mussel-Inspired Adhesive Based on Poly(vinyl alcohol) Backbone"; Macromolecular Chemistry and Physics; v. 218; 2017; p. 1-9.

Zhao, Yanhua et al.; "Bio-inspired reversible underwater adhesive"; Nature Communications: 8:2218; 2017; p. 1-8.

Zhong, Chao et al.; "Strong underwater adhesives made by self-assembling multi-protein nanofibres"; Nature Technology: v. 9; Oct. 2014; p. 858-866.

Extended European Search Report issued in Application No. 19802791.4 dated Jan. 21, 2022, 11 pages.

Florian Ponzio et al., "Robust Alginate-Catechol@Polydopamine Free-Standing Membranes Obtained from the Water/Air Interface", Langmuir, vol. 33, 2017, pp. 2420-2426.

Li Yang et al., "Polydopamine Particles Reinforced Poly(vinyl alcohol) Hydrogel with NIR Light Triggered Shape Memory and Self-Healing Capability", Marcomolecular Rapid Communications, vol. 38, 2017, 8 pages.

Lu Han et al., "Polydopamine Nanoparticles Modulating Stimuli-Responsive PNIPAM Hydrogels with Cell/Tissue Adhesiveness", Applied Materials & Interfaces, vol. 8, 2016, pp. 29088-29100.

Meihong Liao et al., "Wearable, Healabie, and Adhesive epidermal Sensors Assembled from Mussel-Inspired Conductive Hybrid Hydrogel Framework", Advanced Functional Materials, vol. 27, 2017, 11 pages.

* cited by examiner

HIGH PERFORMANCE ADHESIVES; METHODS OF MAKING; AND USE

CROSS-REFERENCE TO RELATED APPLICATION

This application claims the benefit of U.S. Provisional Application No. 62/670,946 filed May 14, 2018, which is hereby incorporated by reference in its entirety.

FIELD

The disclosure is in the general field of high performance adhesives for wet or underwater environments.

BACKGROUND

The design of smart adhesives with high adhesive properties in a wet environment has remained a major challenge. Such adhesive are highly desirable because of their potential applications ranging from functional materials in marine environments to biomedical implants and coatings. Most of the common commercial polymeric adhesives are quickly weakened and easily destroyed in an aqueous environment owing to the formation of hydrated cation layers in water environment, resulting in significant deterioration of the adhesion. Furthermore, current commercial underwater adhesives are very expensive and not environmentally friendly.

There remains a need in the art for new adhesives with high and durable performance for underwater and biomedical applications.

SUMMARY

In an embodiment, an adhesive comprises a first compound comprising three or more 1,2-dihydroxybenzene groups; and a second compound that is a functionalized polymer; wherein the first compound and second compound are in the form of a mixture, and wherein the adhesive has adhesive properties when wet.

In another embodiment, a method of preparing an adhesive comprises mixing in an aqueous solvent, a first compound comprising three or more 1,2-dihydroxybenzene groups; and a second compound that is a functionalized polymer; to form an adhesive having adhesive properties when wet. In a further embodiment is an adhesive prepared by the method.

In another embodiment is an article prepared from the adhesive.

DETAILED DESCRIPTION

Figure 1:
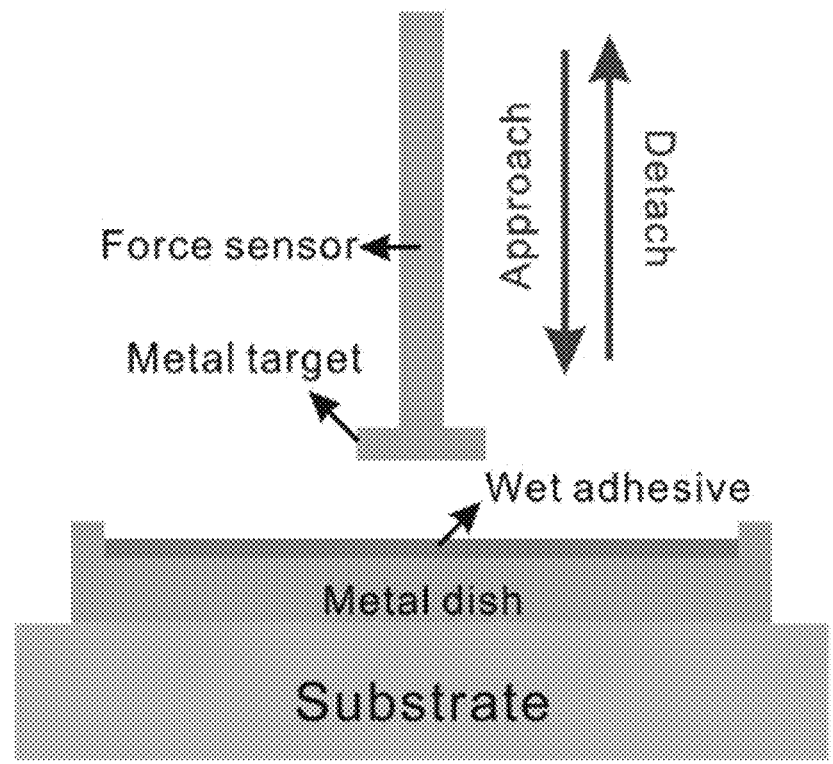
FIG. 1 Schematic of the set-up to characterize the interfacial adhesion.

Described herein are high performance, economical, and environmentally friendly adhesives that function in aqueous environments. The adhesive is inspired by marine animals such as mussels, barnacles, and tube worms, which exhibit excellent underwater adhesion on the rock of sea floor. Among these marine organisms, mussels exhibit unique underwater adhesion via the foot proteins of byssus. It has been verified that the catechol groups from the side chain of the mussel foot proteins is the main contributor to the unique underwater adhesion.

The adhesives described herein having adhesive properties when wet comprise a mixture of a first compound and a second compound, wherein the first compound comprises three or more 1,2-dihydroxybenzene groups; and wherein the second compound is a functionalized polymer comprising one or more functional groups capable of interacting with the first compound through one or more of a covalent bond, hydrogen bonding, electrostatic interactions, hydrophobic interactions, pi-pi interactions, pi-cation interactions, metal coordination, and sulfide-sulfide bonds. Such functional groups include hydroxyl, amine, thiol, carboxyl, ester, amide, and the like, specifically hydroxyl. As defined herein, the functionalized polymer does not comprise a 1,2-dihydroxybenzene group.

Exemplary first compounds comprising 1,2-dihydroxybenzene groups, include polydopamine (PDA); polydopamine derivatives; derivatives of hydrocaffeic acid; poly(caffeic acid); tris(2-aminoethyl)amine (Tren) derivatives, including Tren-lysine-catechol (TLC), Tren-arginine-catechol (TAC), Tren-catechol (TC); poly-(3,4-dihydroxyphenethyl) methacrylamide-co-aminoethylmethacrylamide; poly(dopamine methacrylamide-co-2-methoxyethyl acrylate) (p(DMAm-co-MEA)) and the like, or a combination comprising at least one of the foregoing. Within this embodiment, the polymeric first compounds can have a weight average molecular weight (Mw) of about 1,000 to about 100,000, specifically about 5,000 to about 75,000, and more specifically about 10,000 to about 50,000. In an embodiment, the first compound is PDA, and more specifically PDA having a weight average molecular weight (Mw) of about 1,000 to about 100,000.

Exemplary second compounds include polymers such as polyvinyl alcohol (PVA), polyvinylpyrrolidone (PVP), a polysaccharide, chitosan, a starch, an alginate such as sodium alginate, xanthan, a protein, gelatin, a waterborne polyurethane, a polyacrylamide, a polyacrylic acid, a poly(alkyl)acrylic acid where the alkyl is methyl or ethyl, polyethylenimine, a polyarylate, and the like, or a combination comprising at least one of the foregoing. Specifically, the second compound is a polymer comprising hydroxyl groups such as PVA, polysaccharides, chitosan, starch, sodium alginate, xanthan, and the like, or a combination comprising at least one of the foregoing. In an embodiment, the second compound is a PVA having a weight average molecular weight (Mw) of about 5,000 to about 1,000,000, specifically about 10,000 to about 750,000, more specifically about 50,000 to about 500,000, and still more specifically about 100,000 to about 250,000. In another embodiment, the second compound is polyvinylpyrrolidone ($M_w$ of about 5,000 to about 1,000,000), chitosan ($M_w$ of about 5,000 to about 500,000), waterborne polyurethane ($M_w$ of about 5,000 to about 500,000), starch ($M_w$ of about 5,000 to about 500,000), gelatin ($M_w$ of about 5,000 to about 500,000), protein ($M_w$ of about 5,000 to about 1,000,000), sodium alginate ($M_w$ of about 5,000 to about 1,000,000), and polyacrylamide ($M_w$ of about 5,000 to about 1,000,000).

The weight ratio of first compound to second compound can be as low as 0.01 wt %. Exemplary weight ratios of first compound to second compound can be about 2:1, about 1:1, about 1:2, about 1:5, about 1:10, about 1:20, about 1:30, and about 1:40. The first compound can enhance the adhesion force of the adhesive in wet or underwater environment. By adding different amounts of the first component into the second component solution the weight ratio of composite components can be altered to prepare adhesives with various adhesion strengths.

In an embodiment, an effective adhesive can be prepared by mixing the first compound and the second compound in an aqueous solvent, specifically water and an optional water miscible solvent including an alcohol, specifically a lower alkyl alcohol. In a specific embodiment, the solvent is water free of an organic solvent. Once the mixture is formed, the mixture can be used as an adhesive in its as-prepared liquid form or the water can be removed to leave a dry, solid adhesive material that can be later activated on demand by exposure to moisture.

In an embodiment, the aqueous mixture of first compound and second compound can be formed into an adhesive film, optionally a dried adhesive film prepared by removal of the aqueous solvent. The film can be formed on a substrate by any suitable means including drop casting, spin coating, doctor blade, dip coating, spray coating, screen printing, gravure coating, solution casting, deposition and the like, followed by optional drying at ambient temperature and pressure or under vacuum and or heat to form the dried adhesive film. The adhesive film can be of any pattern or design on a suitable substrate and can be of any desired thickness and size. Exemplary thickness of the dried adhesive film can be from about 1 micrometer to about 1 centimeter, specifically about 250 micrometers to about 5 millimeters, more specifically about 500 micrometers to about 1 millimeter.

The type of substrate suitable for the described adhesives is not particularly limited. Exemplary substrate materials include glass, paper, plastics, metal, ceramics, biological tissues, and the like.

In an embodiment, an effective adhesive can be prepared by mixing polydopamine (PDA) with polyvinyl alcohol (PVA) in an aqueous solvent to form a composite adhesive. The resulting adhesive exhibits a very fast bonding speed and strong adhesion force by simply applying water or moisture. Because both PDA and PVA possess a large number of hydroxyl groups, PDA can be well dispersed with the PVA and the as-prepared composite is of high flexibility. Furthermore, owing to the 3,4-dihydroxy-L-phenylalanine groups in PDA and the hydrophilic properties of the PVA, the PDA/PVA composite exhibits excellent adhesion after applying water on it. The entire process to prepare PDA/PVA adhesive can be free of organic solvent, and the adhesive is environmentally friendly, safe, and biocompatible.

The adhesives find particular application in wet or underwater environments. Although strong, the adhesion also permits rapid detachment and reattachment for many times. The as-prepared polymer mixture, e.g., PVA/PDA, can be dried and used as a solid adhesive.

The disclosed adhesives provide a unique combination of advantages including ease of mass production and transportation; widely available and low cost raw materials; no need for organic solvents; strong adhesion in wet and underwater environments; and excellent conformability on human skin.

In an embodiment, a biocompatible adhesive is prepared from a PDA/PVA mixture. In an embodiment, the adhesive is prepared by mixing polydopamine (PDA)/polyvinyl alcohol (PVA) in an aqueous solvent to form a composite of PDA/PVA composite adhesive.

Approaches to activate the adhesive can be achieved by any known means to apply moisture to the adhesive. Non-limiting examples include spraying water vapor, spraying liquid water, add drops of water to the surface of the adhesive, and the like.

In an embodiment, a solid thin film adhesive comprising the mixture of first compound and second compound as defined herein exhibits excellent adhesion and conformability to human skin, thus having use as a fixation for flexible/stretchable wearable devices and biomedical applications including tissue transplantation, wound coverings, and drug delivery devices.

As PVA, PDA, and water are all environmental friendly, the adhesive prepared from these materials find application in biomedical areas such as tissue transplantation. The PDA/PVA adhesive is both inexpensive and environmentally friendly, and exhibits immediate and strong adhesion underwater.

The wet adhesive can be applied as functional materials in marine environments, high performance glue in commercial package, ocean transportation, tissue transplantation, and medical treatment. The adhesive can be attached and detached from human skin and has good conformability to human skin.

The adhesive can be dried in the form of a solid thin film and used as a solid adhesive for various applications. Dried films of the adhesive can easily be fabricated to any desired thickness or dimension required for a particular application. The solid thin film can generate a strong adhesion upon being wet momentarily. In an embodiment, the solid thin film can be wet to generate high conformability on human skin, and suitable for use to adhere devices for wearable electronics and use in various biomedical applications.

The adhesives can include an optional additive as long as the additive is not substantially detrimental to the adhesive properties of the adhesive in aqueous environments. Exemplary additives include a buffer; a pH modifier; an active agent, not limited to antimicrobials (antibacterial, antifungal, etc.), anti-inflammatories, and the like; colorants; or a combination comprising at least one of the foregoing.

In an embodiment, the adhesive may further comprise an additive such as a salt that can aid in water uptake or assist the adhesive to retain water. The salt additive can be used in varying amounts in order to conveniently and facilely adjust the adhesion strength of the adhesive when wet as the amount of water determines the strength of adhesion. Suitable salt additives include metal-halide salts, for example alkaline or alkaline earth metal-halide salts. Specific examples of such salts include $FeCl_3$, $CaCl_2$), NaCl, KCl, $MgCl_2$, $ZnCl_2$, and the like.

The salt additive may be used in any suitable amount that aids in the improvement of the adhesion of adhesive. In an embodiment, the salt additive may be used in an amount up about 100% weight ratio of salt additive to the second compound that is a functionalized polymer (e.g. PVA), i.e. 100/100; specifically about 1 to about 90%, more specifically about 5 to about 80%, yet more specifically about 10 to about 70%, still more specifically about 20 to about 60%, more specifically about 30 to about 50% weight ratio of salt additive to the second compound.

In an embodiment, the adhesive is used in a biomedical application or as an interface for wearable electronics to be in contact with skin, it is desirable to have the strength of adhesion substantially similar to the stiffness of skin for comfort of the subject. The strength of the adhesion can be adjusted, in part, by the use of a salt additive in the adhesive.

Besides use as a medical adhesive for direct-skin wearable medical technologies including monitoring devices, the adhesive may be used as a cosmetic adhesive material to adhere a cosmetic material or cosmetic device to a person's skin, hair, or nails. The adhesive provides adequate adhesion as well as ease of removal when needed. Exemplary cosmetic devices include false eyelashes, hair extensions, false nails, adherable body jewelry, other body adornments, and the like.

In another embodiment is an adhesive prepared by a process of mixing in an aqueous solvent a first compound comprising three or more 1,2-dihydroxybenzene groups; and a second compound that is a functionalized polymer; to form an adhesive mixture having adhesive properties when wet.

The following non-limiting examples further illustrate various embodiments described herein.

EXAMPLES

Example 1. Procedure for the Preparation of PDA/PVA Adhesive, Wet

A general procedure for the preparation of PDA/PVA composite adhesive is shown in Scheme 1. Dopamine hydrochloride (DA·HCl) (commercially available from vendors such as Alfa Aesar) was dissolved in tris-HCl solution (0.01 M, pH of 8.5) with a concentration of 50 mg/mL (higher concentrations to 100 mg/mL can also be prepared). After spontaneous polymerization for about 12 hours, 2 mL of the as-synthesized PDA solution was added dropwise into 4 mL PVA ($M_w$=167,500)/deionized water solution (50 mg/mL) in a ratio of 1:2 by weight. The prepared PDA/PVA mixture solution can be used directly as an adhesive. Alternatively, the solution can be dried and used as a solid thin film adhesive as described in Example 2.

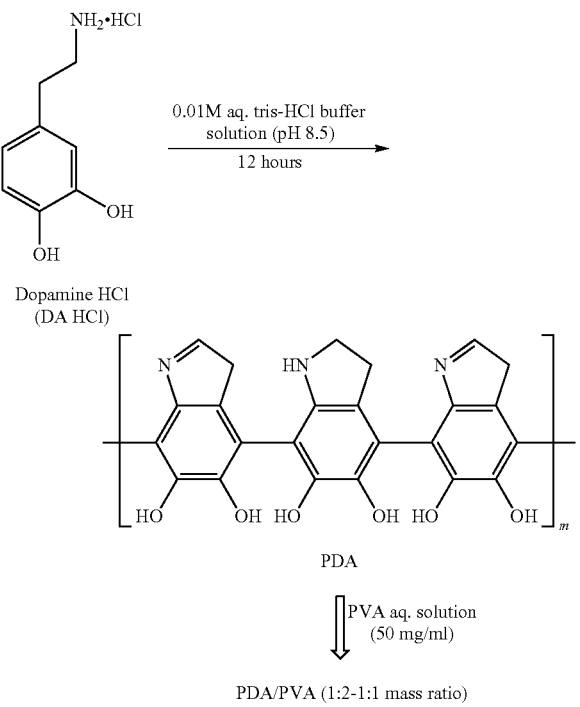

Example 2. Preparation of Dried PDA/PVA Composite Adhesive Film

PDA was homogeneously mixed with PVA to form an aqueous mixture of PDA/PVA composite similar to Example 1. The mixture was allowed to dry in a petri dish to result in the formation of a thin, solid film. The dry composite film can be easily peeled off from the container and transferred to another substrate for use in any suitable adhesive application. The dry composite adhesive is very easy to handle and can be used under many different conditions.

The composite adhesive has no adhesion when it is dry. However, after applying a few drops of water on the surface of a film of the composite adhesive to activate the adhesive, a small glass vial can be easily glued onto the adhesive almost immediately, demonstrating that the adhesive can take effect very fast under a wet environment. Furthermore, when fully immersed in water, the adhesive maintains high adhesion.

The adhesive also exhibits reversible and repeated adhesive capability. To evaluate the repeated adhesion of the adhesive, a small glass vial was first detached from the adhesive film by applying a high external force. After detachment from the adhesive film, the glass vial can be re-adhered onto the adhesive film again by simply pressing it back onto the wet film. Moreover, the detachment and reattachment can be repeated many times, proving the high repeating adhesion of the as-prepared adhesive.

The adhesive film can be allowed to dry to lose its adhesion, but if a little drop of water is applied to the dried film, the adhesive film can function again, performing long term stability.

To further evaluate the adhesion force of the adhesive, a PDA/PVA film (~4.1 cm$^2$) was applied onto a first glass slide. After applying a drop of water, a second glass slide was adhered to the first glass slide with the adhesive film between the two glass slides. The adhesion occurred within several seconds. Furthermore, two glass vials full of water (each one weighing about 40.5 g) were placed on the end of the glass slides, and the slides remained attached securely. In another example, two weights (200 g each) were then placed on the end of the glass slides and the adhesion still did not break. These experiments demonstrate that the adhesive has very high adhesion force.

Owing to the strong adhesion and the ease of transferring the PDA/PVA film, the dried film can be easily peeled off from the polystyrene dish and transferred onto human skin after applying a few drops of water on the skin. The adhesive can be well attached onto human skin and has a good conformability to human skin upon flexing and stretching, demonstrating that the as-prepared PDA/PVA adhesive film has a great potential in biomedical and wearable device applications.

Figure 2:
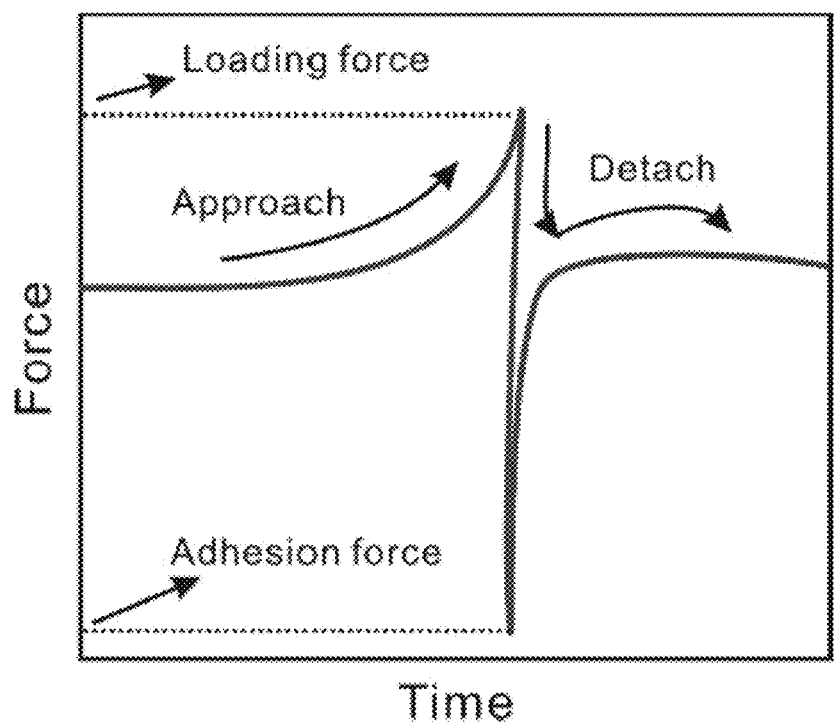
FIG. 2 Schematic drawing showing a representative adhesion force curve.

Example 3. Adhesion Force Testing; Dynamic Shear Strength; and Peel Strength for PDA/PVA Composite Adhesive Film The dynamic shear strength was tested using a Chemsultants DS-1000 testing equipment by gluing different substrates (PET and PLA substrates), with the composite adhesive film coating on them in a thickness of ca. 100 μm) on a 5 lb rubber-coated steel roller with a shearing speed of 0.05"/min. The peel strength was tested using a Labthink XC-ECW testing equipment by gluing different substrates (PET and PLA substrates), with adhesives (PVA:PDA=2:1) coating on them in a thickness of ca. 100 μm) on a 5 lb rubber-coated steel roller with a peeling speed of 12"/min. The adhesion force testing was carried out at room temperature using a tensile testing machine (KJ-1065A, Dongguan Kejian Instruments Co., Ltd. China, see FIG. 1 for a schematic of the set-up and FIG. 2 for a representative adhesion force curve). All the films used for adhesion test have a 70% weight ratio of $FeCl_3$ to PVA (7/10) and were pre-stored under 70% relative humidity (RH) for 24 hours before testing.

Table 1 provides the results of adhesion force of PVA/PDA-$Fe^{3+}$ wet film as a function of PVA/PDA ratio.

TABLE 1

Adhesion force as a function of PVA/PDA ratio. The loading force was 1 kPa.

| PVA/PDA mass ratios | Adhesion Force (kPa) |
| --- | --- |
| 2:1 | 9.6 |
| 5:1 | 6.7 |
| 10:1 | 5.6 |
| 20:1 | 4.9 |
| 50:1 | 4.4 |

Table 2 provides the results of adhesion force of the PVA/PDA-$Fe^{3+}$ wet film as a function of loading force.

TABLE 2

Adhesion force as a function of loading force. The PVA/PDA ratio was 2:1.

| Loading Force (kPa) | Adhesion Force (kPa) |
| --- | --- |
| 1 | 9.5 |
| 4 | 14.1 |
| 10 | 17.8 |
| 20 | 24.0 |
| 40 | 30.2 |

Table 3 provides the dynamic shear strength and peel strength of the wet adhesive film to different substrates (PET and PLA).

TABLE 3

| Substrate | Dynamic shear strength (kPa) | Peel strength (N/m) |
| --- | --- | --- |
| PET | 44.1 | 60.1 |
| PLA | 55.8 | 68.9 |

The adhesives, uses thereof, and methods disclosed herein include(s) at least the following aspects:

Aspect 1: An adhesive, comprising a first compound comprising three or more 1,2-dihydroxybenzene groups; and a second compound that is a functionalized polymer; wherein the first compound and second compound are in the form of a mixture, and wherein the adhesive has adhesive properties when wet.

Aspect 2: The adhesive of Aspect 1, wherein the first compound and the second compound are in a weight ratio of about 2:1, about 1:1, about 1:2, about 1:5, about 1:10, about 1:20, about 1:30, or about 1:40.

Aspect 3: The adhesive of Aspect 1 or 2, wherein the first compound is polydopamine (PDA); a polydopamine derivative; a derivative of hydrocaffeic acid; poly(caffeic acid); a tris(2-aminoethyl)amine (Tren) derivatives, including Tren-lysine-catechol (TLC), Tren-arginine-catechol (TAC), Tren-catechol (TC); or a combination comprising at least one of the foregoing, wherein the polymeric first compound can have a weight average molecular weight (Mw) of about 1,000 to about 100,000; specifically the first compound is PDA; and more specifically PDA having a weight average molecular weight (Mw) of about 1,000 to about 100,000.

Aspect 4: The adhesive of any one of Aspects 1-3, wherein the second compound is polyvinyl alcohol (PVA), polyvinylpyrrolidone (PVP), a polysaccharide, chitosan, a starch, an alginate such as sodium alginate, xanthan, a protein, gelatin, a waterborne polyurethane, a polyacrylamide, a polyacrylic acid, a poly(alkyl)acrylic acid where the alkyl is methyl or ethyl, polyethylenimine, a polyarylate, or a combination comprising at least one of the foregoing; specifically, the second compound is a polymer comprising hydroxyl groups such as PVA, polysaccharides, chitosan, starch, sodium alginate, xanthan, or a combination comprising at least one of the foregoing; more specifically the second compound is a PVA having a weight average molecular weight (Mw) of about 5,000 to about 1,000,000, polyvinylpyrrolidone having a weight average molecular weight (Mw) of about 5,000 to about 1,000,000, chitosan having a weight average molecular weight (Mw) of about 5,000 to about 500,000, waterborne polyurethane having a weight average molecular weight (Mw) of about 5,000 to about 500,000, starch having a weight average molecular weight (Mw) of about 5,000 to about 500,000, gelatin having a weight average molecular weight (Mw) of about 5,000 to about 500,000, protein having a weight average molecular weight (Mw) of about 5,000 to about 1,000,000, sodium alginate having a weight average molecular weight (Mw) of about 5,000 to about 1,000,000, and polyacrylamide having a weight average molecular weight (Mw) of about 5,000 to about 1,000,000.

Aspect 5: The adhesive of any one of Aspects 1-4, wherein the adhesive further comprises a salt additive in an amount to increase the adhesion of the adhesive.

Aspect 6: The adhesive of Aspect 5, wherein the salt additive is a metal-halide salt.

Aspect 7: The adhesive of any one of Aspects 1-6, wherein the adhesive is in the form of a wet or dry film.

Aspect 8: The adhesive of any one of Aspects 1-6, wherein the adhesive is in the form of a dry film that can be activated with water.

Aspect 9: A method of preparing an adhesive, comprising mixing in an aqueous solvent, a first compound comprising three or more 1,2-dihydroxybenzene groups; and a second compound that is a functionalized polymer; to form an adhesive having adhesive properties when wet.

Aspect 10: The method of Aspect 9, wherein the first compound and the second compound are in a weight ratio of about 2:1, about 1:1, about 1:2, about 1:5, about 1:10, about 1:20, about 1:30, or about 1:40.

Aspect 11: The method of Aspect 9 or 10, wherein the first compound is polydopamine (PDA); a polydopamine derivative; a derivative of hydrocaffeic acid; poly(caffeic acid); a tris(2-aminoethyl)amine (Tren) derivatives, including Tren-lysine-catechol (TLC), Tren-arginine-catechol (TAC), Tren-catechol (TC); or a combination comprising at least one of the foregoing, wherein the polymeric first compound can have a weight average molecular weight (Mw) of about 1,000 to about 100,000; specifically the first compound is PDA; and more specifically PDA having a weight average molecular weight (Mw) of about 1,000 to about 100,000.

Aspect 12: The method of any one of Aspects 9-11, wherein the second compound is polyvinyl alcohol (PVA), polyvinylpyrrolidone (PVP), a polysaccharide, chitosan, a starch, an alginate such as sodium alginate, xanthan, a protein, gelatin, a waterborne polyurethane, a polyacrylamide, a polyacrylic acid, a poly(alkyl)acrylic acid where the alkyl is methyl or ethyl, polyethylenimine, a polyarylate, or a combination comprising at least one of the foregoing; specifically, the second compound is a polymer comprising hydroxyl groups such as PVA, polysaccharides, chitosan, starch, sodium alginate, xanthan, or a combination comprising at least one of the foregoing; more specifically the second compound is a PVA having a weight average molecular weight (Mw) of about 5,000 to about 1,000,000, polyvinylpyrrolidone having a weight average molecular weight (Mw) of about 5,000 to about 1,000,000, chitosan having a weight average molecular weight (Mw) of about 5,000 to about 500,000, waterborne polyurethane having a weight average molecular weight (Mw) of about 5,000 to about 500,000, starch having a weight average molecular weight (Mw) of about 5,000 to about 500,000, gelatin having a weight average molecular weight (Mw) of about 5,000 to about 500,000, protein having a weight average molecular weight (Mw) of about 5,000 to about 1,000,000, sodium alginate having a weight average molecular weight (Mw) of about 5,000 to about 1,000,000, and polyacrylamide having a weight average molecular weight (Mw) of about 5,000 to about 1,000,000.

Aspect 13: The method of any one of Aspects 9-12, wherein the adhesive further comprises a salt additive in an amount to increase the adhesion of the adhesive.

Aspect 14: The method of Aspect 13, wherein the salt additive is a metal-halide salt.

Aspect 15: The method of any one of Aspects 9-14, wherein the adhesive is in the form of a wet or dry film.

Aspect 16: The method of any one of Aspects 9-15, wherein the adhesive is in the form of a dry film that can be activated with water.

Aspect 17: The method of any one of Aspects 9-16, wherein the adhesive can be formed into a film by drop casting, spin coating, doctor blade, dip coating, spray coating, screen printing, gravure coating, solution casting, and deposition, optionally followed by a drying step.

Aspect 18: The method of Aspect 17, wherein the dried film has a thickness of about 1 micrometer to about 1 centimeter, specifically about 250 micrometers to about 5 millimeters, more specifically about 500 micrometers to about 1 millimeter.

Aspect 19: An adhesive prepared by the method of any one of Aspects 9-18.

Aspect 20: An article prepared from the adhesive of any one of Aspects 1-8 or 19, for use as a fixation for wearable devices and biomedical applications including tissue transplantation, wound coverings, and drug delivery devices; or for use as a cosmetic adhesive.

While the invention has been described with reference to exemplary embodiments, it will be understood by those skilled in the art that various changes may be made and equivalents may be substituted for the elements thereof without departing from the scope of the invention. In addition, many modifications may be made to adapt the teaching of the invention to particular use, application, manufacturing conditions, use conditions, composition, medium, size, and/or materials without departing from the essential scope and spirit of the invention. Therefore, it is intended that the invention not be limited to the particular embodiments and best mode contemplated for carrying out this invention as described herein, but that the invention will include all embodiments falling within the scope of the appended claims.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting of the true scope of the invention disclosed herein. It is also to be understood that the terminology used herein is for the purpose of describing particular embodiments only, and is not intended to be limiting. Since many modifications, variations, and changes in detail can be made to the described examples, it is intended that all matters in the preceding description and shown in the accompanying figures be interpreted as illustrative and not in a limiting sense.

All ranges disclosed herein directed to the same component or property are inclusive of the endpoints, and the endpoints are independently combinable with each other. Each range disclosed herein constitutes a disclosure of any or all intermediate points or sub-range lying within the disclosed range.

The use of the terms "a" and "an" and "the" and words of a similar nature in the context of describing the improvements disclosed herein (especially in the context of the following claims) are to be construed to cover both the singular and the plural, unless otherwise indicated herein or clearly contradicted by context. The term "or" means "and/or" unless clearly indicated otherwise by context. Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. In general, the compositions or methods may alternatively comprise, consist of, or consist essentially of, any appropriate components or steps herein disclosed. The invention may additionally, or alternatively, be formulated so as to be devoid, or substantially free, of any components, materials, ingredients, adjuvants, or species, or steps used in the prior art compositions or that are otherwise not necessary to the achievement of the function and/or objectives of the present claims. "Optional" or "optionally" means that the subsequently described event or circumstance may or may not occur, and that the description includes instances where the event occurs and instances where it does not. Unless specified to the contrary herein, all test standards are the most recent standard in effect at the time of filing this application.

The terms "first," "second," and the like, "primary," "secondary," and the like, as used herein do not denote any order, quantity, or importance, but rather are used to distinguish one element from another. The term "combination" is inclusive of blends, mixtures, alloys, reaction products, and the like. Unless defined otherwise, technical and scientific terms used herein have the same meaning as is commonly understood by one of skill in the art to which this invention belongs.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

The modifier "about" used in connection with a quantity is inclusive of the stated value and has the meaning dictated by the context (e.g., it includes, at a minimum the degree of error associated with measurement of the particular quantity).

All methods described herein can be performed in any suitable order unless otherwise indicated herein or otherwise clearly contradicted by context. The use of any and all examples, or exemplary language (e.g., "such as"), is intended merely to better illustrate the invention and does not pose a limitation on the scope of the invention or any embodiments unless otherwise claimed.

The invention claimed is:

1. An adhesive, comprising:
   a first compound comprising three or more 1,2-dihydroxybenzene groups; and
   a second compound that is a functionalized polymer;
   wherein the first compound and second compound are in the form of a mixture in a weight ratio of about 2:1 to about 1:30, and
   wherein the adhesive is in the form of a dry film that can be activated with water.

2. The adhesive of claim 1, wherein the first compound and the second compound are in a weight ratio of about 2:1, about 1:1, about 1:2, about 1:5, about 1:10, about 1:20, or about 1:30.

3. The adhesive of claim 1, wherein the first compound is polydopamine (PDA); a polydopamine derivative; poly(caffeic acid); a tris(2-aminoethyl)amine (Tren) derivatives; or a combination comprising at least one of the foregoing.

4. The adhesive of claim 1, wherein the second compound is polyvinyl alcohol (PVA), polyvinylpyrrolidone (PVP), a polysaccharide, chitosan, a starch, an alginate, xanthan, a protein, gelatin, a waterborne polyurethane, a polyacrylamide, a polyacrylic acid, a poly(alkyl)acrylic acid where the alkyl is methyl or ethyl, polyethylenimine, a polyarylate, or a combination comprising at least one of the foregoing.

5. The adhesive of claim 1, wherein the adhesive further comprises a salt additive in an amount to increase the adhesion of the adhesive.

6. The adhesive of claim 5, wherein the salt additive is a metal-halide salt.

7. A method comprising:
   mixing in an aqueous solvent
   a first compound comprising three or more 1,2-dihydroxybenzene groups; and
   a second compound that is a functionalized polymer;
   to form an adhesive film having adhesive properties wherein the first compound and second compound are in the form of a mixture in a weight ratio of about 2:1 to about 1:30, wherein the adhesive is in the form of a dry film that can be activated with water.

8. The method of claim 7, wherein the first compound and the second compound are in a weight ratio of about 2:1, about 1:1, about 1:2, about 1:5, about 1:10, about 1:20, or about 1:30.

9. The method of claim 7, wherein the first compound is polydopamine (PDA); a polydopamine derivative; poly(caffeic acid); a tris(2-aminoethyl)amine (Tren) derivatives; or a combination comprising at least one of the foregoing.

10. The method of claim 7, wherein the second compound is polyvinyl alcohol (PVA), polyvinylpyrrolidone (PVP), a polysaccharide, chitosan, a starch, an alginate, xanthan, a protein, gelatin, a waterborne polyurethane, a polyacrylamide, a polyacrylic acid, a poly(alkyl)acrylic acid where the alkyl is methyl or ethyl, polyethylenimine, a polyarylate, or a combination comprising at least one of the foregoing.

11. The method of claim 7, wherein the adhesive further comprises a salt additive in an amount to increase the adhesion of the adhesive.

12. The method of claim 11, wherein the salt additive is a metal-halide salt.

13. The method of claim 7, wherein the adhesive is formed into the dry film by drop casting, spin coating, doctor blade, dip coating, spray coating, screen printing, gravure coating, solution casting, deposition and drying to form the dried film.

14. The method of claim 13, wherein the dried film has a thickness of about 1 micrometer to about 1 centimeter.

15. The adhesive prepared by the method of claim 7.

* * * * *